United States Patent [19]

Kleine-Homann

[11] Patent Number: 4,814,509
[45] Date of Patent: Mar. 21, 1989

[54] PREPARATION OF PURE 2,2-DIMETHYL-1,3-PROPANEDIOL

[75] Inventor: Walter Kleine-Homann, Dülmen, Fed. Rep. of Germany

[73] Assignee: Hüls Aktiengesellschaft, Marl, Fed. Rep. of Germany

[21] Appl. No.: 91,863

[22] Filed: Sep. 1, 1987

[30] Foreign Application Priority Data

Nov. 11, 1986 [DE] Fed. Rep. of Germany ....... 3638496

[51] Int. Cl.$^4$ ...................... C07C 29/74; C07C 31/20
[52] U.S. Cl. .................................................... 568/854
[58] Field of Search ......................................... 568/854

[56] References Cited

U.S. PATENT DOCUMENTS

| 2,292,926 | 8/1942 | Brubaker et al. | 568/854 |
| 2,333,696 | 11/1943 | Bludworth | 568/854 |
| 2,400,724 | 5/1946 | Walker | 568/854 |
| 2,778,858 | 1/1957 | Meinhofer | 568/854 |
| 2,865,819 | 12/1958 | Hagemeyer et al. | 568/854 |
| 4,250,337 | 2/1981 | Hausen et al. | 568/854 |

FOREIGN PATENT DOCUMENTS 2045668  3/1972  Fed. Rep. of Germany ...... 568/854

*Primary Examiner*—J. E. Evans
*Attorney, Agent, or Firm*—Gilbert L. Wells

[57] ABSTRACT

Crude 2,2-dimethyl-1,3-propanediol (NPG) is distilled in the presence of sulfuric acid, phosphoric acid or a mixture thereof, with the pH value being set between 6.5 and 7.5, preferably between 6.9 and 7.1 to prepare pure 2,2-dimethyl-1,3-propanediol.

3 Claims, No Drawings

PREPARATION OF PURE 2,2-DIMETHYL-1,3-PROPANEDIOL

CROSS-REFERENCE TO RELATED APPLICATIONS

Applicant claims priority under 35 USC 119 for application No. P 36 38 496.8 filed Nov. 11, 1986 in West Germany.

The disclosure of copending application Ser. No. 07/091,866 of the same inventor as the present application filed on the same day as the present application and entitled, "Process for Lowering the Salt Content in Crude Hydroxy Pivalic Aldehyde" is incorporated herein.

BACKGROUND OF THE INVENTION

The field of the invention is the preparation of 2,2-dimethyl-1,3-propanediol from hydroxy pivalic aldehyde.

Hydroxy pivalic aldehyde is a preliminary state in the production of 2,2-dimethyl-1,3-propanediol, otherwise known as neopentylglycol. Hydroxy pivalic anhydride is reacted both by catalytic reduction and by the Cannizzaro reaction of the aldehyde to form 2,2-dimethyl-1,3-propanediol. The catalysts used in the hydrogenation include, besides Ni, catalysts as disclosed in U.S. Pat. No. 2,400,724, also copper chromites as disclosed in British Pat. No. 1,017,618.

In addition to alkali metal compounds, further alkali earth metal compounds and amines have been described as useful in the aldolization of isobutyraldehyde and formaldehyde.

The salt contents of organic acids is of utmost significance in preparing pure 2,2-dimethyl-1,3-propanediol (neopentylglycol) by distillation. On account of the presence of these salts, the required high temperature of distillation entails dissociation, or resinification of the desired diol. On the one hand, this means substantial losses of product and on the other hand, only an impure diol is obtained. The presence of such salts illustratively alkali/alkali earth/ammonium formiates, isobutyrates or hydroxypivalates can be explained for instance by the Cannizzaro reaction or the presence of traces of oxygen during aldolization.

The state of the art of removing salts from hydrogenation outputs may be ascertained by reference to U.S. Pat. No. 2,865,819; West German Patent Publications No. 967,552; 1,052,383 and 2,045,668 and Japanese Patent No. 69/10767 the disclosures of which are incorporated herein by reference.

The state of the art of aldolization of isobutyraldehyde and formaldehyde to hydroxy pivalic aldehyde and the preparation of neopentylglycol from hydroxy pivalic aldehyde may be ascertained by reference to U.S. Pat. No. 4,250,337 the disclosure of which is incorporated herein by reference.

In the method of Japanese Patent No. 69/10767, the use of extractants such as di-n-butylether is recommended. Also, pretreatment of the hydrogenation output using a thin-film-evaporator is recommended to separate salts and substances of higher boiling points accumulating during synthesis. In U.S. Pat. No. 2,865,819, the salts are removed by adding water and Tetralin and subsequent multi-stage reprocessing by distillation. In West German Published Application No. 1,052,383, polyvalent alcohols are recovered from their aqueous, salt-containing solutions by a quasi "steam distillation" using a thin film evaporator. The use of phosphoric acid is described in West German Patent No. 2,045,668. Again, the use of ion exchangers to treat the "raw product" is described in West German Patent No. 967,552.

Most of the procedures discussed are quite costly because, besides a multistage distillation of the raw product, illustratively also drying and crystallization stages must be carried out or a final aftertreatment with ion exchangers is required. Even the treatment with phosphoric acid according to West German Patent No. 2,045,668 does not permit processing the crude 2,2-dimethyl-1,3-propanediol solution which is extensively free from dissociation. While Applicant's own lab procedures show that the dissociation rate can be decreased, it remains nevertheless significant.

Therefore, a long felt need exists to create a process whereby 2,2-dimethyl-1,3-propanediol is isolated from the raw product in simple and salt free manner without significant dissociation losses.

SUMMARY OF THE INVENTION

Having in mind the limitations of the prior art, it is an object of the present invention to provide a process for isolating 2,2-dimethyl-1,3-propanediol from the raw product of the manufacture from hydroxy pivalic anhydride in simple and salt free manner without significant dissociation losses.

Crude 2,2-dimethyl-1,3-propanediol is purified by adding sulfuric acid, phosphoric acid or a mixture thereof sufficient to set a pH value between 6.5 and 7.5 and then carrying out a distillation to produce pure 2,2-dimethyl-1,3-propanediol.

DESCRIPTION OF THE PREFERRED EMBODIMENTS

Surprisingly, 2,2-dimethyl-1,3propanediol is isolated in problem free manner from the raw product when the raw product is set to a pH value of 6.5 to 7.5, preferably 6.9 to 7.1, by adding sulfuric acid, phosphoric acid or a mixture thereof before distillation. Where it is necessary for the pH value to be kept constant, the pH is maintained by resupplying sulfuric acid and/or phosphoric acid. Any salts precipitated following the addition of sulfuric acid and/or phosphoric acid are separated and thereupon the raw product is processed by distillation.

The treatment with sulfuric acid and/or phosphoric acid may be carried out in the presence of a solvent. Illustratively, suitable solvents are alcohols such as isobutanol, or mixtures thereof.

The process of the invention permits adding the acid both to the crude 2,2-dimethyl-1,3-propanediol (neopentylglycol); illustratively, the acids are dissolved in isobutanol/H$_2$O and after a most extensive topping of the solvents. Even raw products with high salt concentrations can be processed in problem free manner by the process of the invention. The sulfuric acid and/or phosphoric acid used can be both commercial, concentrated or diluted acids. The proportion of dissolved salts is lowered when concentrated rather than dilute acids are used. As shown by Comparison Example D, other acids, for instance hydrochloric acid, are unsuitable.

The acid can be dosed for instance both at room temperature and at higher temperatures, illustratively from 10° to 140° C. For reasons of conservation of energy, the raw product preferably is left at the naturally determined temperature. As a rule, such a temperature should be selected at which the 2,2-dimethyl-1,3-propanediol is present in dissolved form or as a melt depending on the concentration.

Advantageously, any precipitated salts are separated in conventional manner, for instance by using filters or separators.

The desired high purity is achieved by the steps of the process both in discontinuous and in continuous processing which results in the end product.

Preferably, pure 2,2-dimethyl-1,3-propanediol is used as a bifunctional polyester component.

EXAMPLES

COMPARISON EXAMPLE A

The input is a raw product having a content in 2,2-dimethyl-1,3-propanediol of 56% and a sodium content of 480 ppm as prepared by Example 2 of U.S. Pat. No. 4,250,337.

After 500 g of the above product have been fractionated in a 0.5 m column equipped with mesh packings at a pressure of 300 mbars, 322 g of a "main run" are obtained which has a purity of only 54%. Accordingly, 38% of the 2,2-dimethyl-1,3-propanediol contained in the raw product did dissociate.

COMPARISON EXAMPLE B

Under the same conditions as in Comparison Example A, a raw product having a content in 2,2-dimethyl-1,3-propanediol of 50.9% and a sodium content of 260 ppm is processed. Following fractionation, 247 g of an 86% main run are isolated. Accordingly, the dissociation is 16.5%.

COMPARISON EXAMPLE C

When the raw product used in Comparison Example A is treated in the manner of West German Pat. No. 2,045,668 (Examples 2, 4) with 5% phosphoric acid (referred to the sodium content with an excess of 4% of the amount required to form $Na_3PO_4$), then, for the same conditions of distillation, 271 g are isolated as the main run with a purity of 98.0%. Accordingly, 5.1% of the 2,2-dimethyl-1,3-propanediol contained in the raw product dissociated during distillation.

COMPARISON EXAMPLE D

When 10% hydrochloric acid is added to the raw product used in Comparison Example A to adjust the pH value to 7.0%, 277 g of a 94% main run is obtained after distillation. Accordingly, 7% of the 2,2-dimethyl-1,3-propanediol is dissociated during processing.

EXAMPLE 1

500 g of a 56% 2,2-dimethyl-1,3-propanediol raw product having an Na content of 480 ppm and prepared by Example 2 of U.S. Pat. No. 4,250,337 are adjusted by addition of concentrated sulfuric acid to a pH value of 6.5 and following filtration of the precipitate are fractionated in a 0.5 m glass column equipped with mesh packings at a vacuum of 300 mbars. 277 g of 2,2-dimethyl-1,3-propanediol with a purity of 99.0% are then isolated as the main run. The calculated dissociation is 2%. The acid number in the main run is 0.14.

EXAMPLE 2

Retaining the conditions of Example 1, a raw product adjusted to a pH value of 6.9 by means of 50% $H_2SO_4$ is processed. The main run is 279 g with 99.8% pure 2,2-dimethyl-1,3-propanediol, from which the dissociation is calculated to be 0.6%. The acid number of the main run is 0.02.

EXAMPLE 3

The input is 500 g of a raw product with a 2,2-dimethyl-1,3-propanediol content of 50.9% and a sodium content of 260 ppm. A pH value of 6.9 is set by adding concentrated sulfuric acid. The remaining processing is as in Example 1. 280 g of 2,2-dimethyl-1,3-propanediol with a purity of 99.5% and an acid number of 0.03 are isolated as the main run. Accordingly, the dissociation is 0.5%.

EXAMPLE 4

500 g of a 50.5% 2,2-dimethyl-1,3-propanediol raw product with a sodium content of 70 ppm are set by addition of 5% sulfuric acid to a pH value of 7.1 and fractionated as described in Example 1. 252 g of a main run of 99.7% pure 2,2-dimethyl-1,3-propanediol and an acid number of 0.02 are isolated. The calculated dissociation is 0.5%.

I claim:

1. In the process for preparing a 2,2-dimethyl-1,3-propanediol product from hydroxy pivalic aldehyde, the improvement comprising:
    purifying said product by adding an acid selected from the group consisting of sulfuric, phosphoric and mixutures thereof sufficient to set a pH value between 6.5 and 7.5 and precipitating salts from said product and acid, separating said salts,
    carrying out a fractional distillation of said product and acid and separating 2,2-dimethyl-1,3-propanediol.

2. The process of claim 1, wherein said pH is 6.9 to 7.1.

3. The process of claim 1, wherein said acid is sulfuric.

* * * * *